(12) United States Patent
Brammer, Jr. et al.

(10) Patent No.: US 7,829,738 B1
(45) Date of Patent: Nov. 9, 2010

(54) PRODUCTION OF N,N-DIALKLYLAMINOETHYL (METH)ACRYLATES

(75) Inventors: Larry E. Brammer, Jr., Kingsport, TN (US); Barbara E. Fair, Lisle, IL (US); Cheng-Sung Huang, Naperville, IL (US); Linh Quach, Arlington Heights, IL (US); Peter E. Reed, Plainfield, IL (US); Leonard M. Ver Vers, Downers Grove, IL (US)

(73) Assignee: Nalco Company, Naperville, IL (US)

( * ) Notice: Subject to any disclaimer, the term of this patent is extended or adjusted under 35 U.S.C. 154(b) by 0 days.

(21) Appl. No.: 12/468,585

(22) Filed: May 19, 2009

(51) Int. Cl.
*C07C 69/52* (2006.01)
(52) U.S. Cl. .................................... 560/222
(58) Field of Classification Search ........................ None
See application file for complete search history.

(56) References Cited

U.S. PATENT DOCUMENTS 6,417,392 B1 * 7/2002 Nagano et al. .............. 560/222
6,437,173 B1 * 8/2002 Hurtel et al. ................ 560/217

FOREIGN PATENT DOCUMENTS

| CN | 201424446 | | 3/2010 |
| JP | 62201852 | * | 9/1987 |
| JP | 11222469 | * | 8/1999 |
| JP | 11246495 | * | 9/1999 |
| JP | 2001172234 | * | 6/2001 |

* cited by examiner

*Primary Examiner*—Karl J Puttlitz
(74) *Attorney, Agent, or Firm*—Benjamin E. Carlsen; Michael B. Martin

(57) ABSTRACT

A method and apparatus for preparing a N,N-dialkylaminoalkyl acrylate in a continuous transesterification reaction. The reaction involves adding alkyl acrylates such as methacrylate or ethacrylate to a reboiler mechanism and efficiently removing alcohol co-products. Because the reaction is continuous, the alkyl acrylates can be added as needed to increase output, decrease output, or fine-tune the reaction dynamics. An entrainer is used to form a volatile azeotrope which contains both alcohol and entrainer and which is easily removed from the reboiler mechanism. This method reduces the amount of entrainer needed per unit of alkyl acrylate used and eliminates any need to purify the end product from entrainer contamination of the resulting N,N-dialkylaminoalkyl acrylate product.

12 Claims, 1 Drawing Sheet

PRODUCTION OF N,N-DIALKLYLAMINOETHYL (METH)ACRYLATES

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

This invention relates to a continuous process for preparing N,N-dialkylaminoalkyl (meth)acrylates by transesterification of an alkyl (meth)acrylate with a dialkylamino alcohol in the presence of catalyst and entrainer to form the N,N-dialkylaminoalkyl (meth)acrylate and byproduct alcohol in which an azeotropic mixture of entrainer and byproduct alcohol is continuously removed from the transesterification, to equipment for performing the transesterification and to equipment and methods for purifying the N,N-dialkylaminoalkyl (meth)acrylate.

A number of previous approaches have been taken for preparing N,N-dialkylaminoalkyl (meth)acrylates. In Japanese Patent Application 2001/172234 A2 a hexane entrainer is used in a series of distillation towers which is washed with water, separated in a decanter, and returned to a column. In Japanese Patent Application 2001/172235 number of serial reaction towers are used with purification column, in Japanese Patent Application 2001/172236 A two columns are used, one which removes excess methyl acrylate and one which removes excess DMAE from the catalyst and other heavy components with an evaporator, US Published Patent Application 2004/0168903 A1 describes using 3 or 4 distillation columns that sequentially react then separate the products, US Published Patent Application 2004/0171868 A1 describes a process in which lower alcohol co-products are removed along with lower (meth) acrylate and is then fed into a plant to convert the alcohol co-products back into methyl acrylate, U.S. Pat. No. 6,437,173 describes using a titanium catalyst along with three distillation columns, Published PCT Application WO 2003/093218 A1 describes a tubular piston reaction technology, U.S. Pat. No. 6,417,392 describes removing alcohol co-products as (meth)acrylate azeotropes, Published PCT Application WO 2007/057120 A1 describes a useful entrainer, Japanese Patent Application 2004/189650 A2 describes a batch process, and Japanese Patent Application 2004/106278 A1 describes a batch process which uses water to facilitate the Michael adduct decomposition.

Despite all of these attempts however there is still a need for a simple cost, effective, high yield method of preparing N,N-dialkylaminoalkyl (meth)acrylates that is a continuous reaction that allows users to add reagents and catalysts to the ongoing reaction as desired.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

BRIEF SUMMARY OF THE INVENTION

At least one embodiment is directed towards a method of preparing a N,N-dialkylaminoalkyl acrylate of Formula 1:

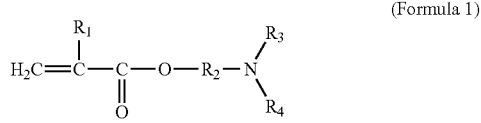

(Formula 1)

wherein $R_1$ is H, or $C_1$-$C_4$ alkyl; $R_2$ is $C_1$-$C_4$ alkylene; and $R_3$ and $R_4$ are $C_1$-$C_4$ alkyl. The method comprises:

a) Providing a distillation reactor comprising a distillation column and a reboiler.

b) Continuously adding to the distillation column, entrainer, catalyst, polymerization inhibitor(s), and an alkyl acrylate of Formula 2

(Formula 2)

wherein $R_5$ is $C_1$-$C_4$ alkyl and a dialkylamino alcohol is of Formula 3.

(Formula 3)

The continuous addition occurs under conditions resulting in the transesterification of the alkyl acrylate with said dialkylamino alcohol to form said N,N-dialkylaminoalkyl acrylate and an alcohol of formula $R_5OH$. The method also comprises:

c) Simultaneously removing an azeotropic mixture of the entrainer and the alcohol from the distillation column and removing the N,N-dialkylaminoalkyl acrylate and residual reactants from the reboiler.

At least one embodiment is directed to a method in which $R_1$ is H or methyl, $R_2$ is ethylene and $R_3$, $R_4$ and $R_5$ are methyl. The entrainer may be selected from the list consisting of methylpentane, hexane, heptane, C4-C8 straight chain hydrocarbons, C4-C8 cyclic hydrocarbons, C4-C8 branched hydrocarbons, and any combination thereof. The catalyst may be one item selected from the list consisting of strong acids, strong bases, tin-based Lewis acids, titanium based Lewis acids, and tin catalysts that exist as liquids at room temperature and which are highly soluble in the reaction medium, di-N-butyltin diacetae (DBTA), and any combination thereof. The entrainer, catalyst, inhibitor, dialkylamino alcohol and alkyl acrylate may all be added to the reboiler. The entrainer, catalyst, inhibitor and dialkylamino alcohol may also be added to the distillation column and the alkyl acrylate is added to the reboiler. In addition, the molar feed ratio of methyl acrylate to N,N-dimethylaminoethanol may be less than or equal to 1.7, and the chemical conversion of N,N-dimethylaminoethanol to N,N-dimethylaminoethyl acrylate may be greater than 88%.

At least one embodiment is directed to a method in which the distillation column comprises between 1 and 40 distillation trays arranged sequentially from a bottom of the column to a top of a column. In addition, one item selected from the list of the entrainer, the catalyst, and the polymerization inhibitor, and any combination thereof are fed into the distillation column at a position lower than a middlemost distillation tray. At least one embodiment is directed to a method in which there is substantially no entrainer mixed with the N,N-dialkylaminoalkyl acrylate when the N,N-dialkylaminoalkyl acrylate is removed from the reboiler.

BRIEF DESCRIPTION OF THE DRAWINGS

A detailed description of the invention is hereafter described with specific reference being made to the drawings in which.

DETAILED DESCRIPTION OF THE INVENTION

Figure 1:
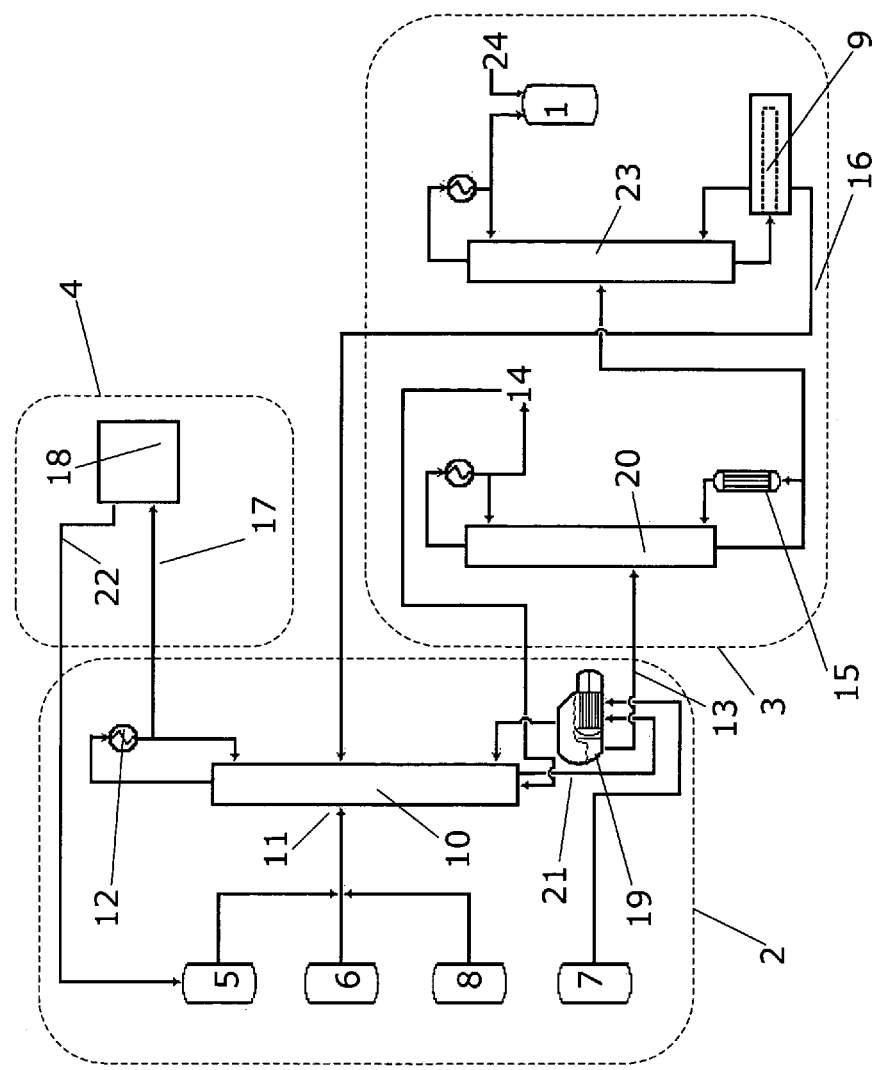
FIG. 1 is an illustration of a process of preparing N,N-dialkylaminoalkyl acrylate.

"Alkyl" means a monovalent group derived from a straight or branched chain saturated hydrocarbon by the removal of a single hydrogen atom. Representative alkyl groups include methyl, ethyl, n- and iso-propyl, n-, sec-, iso- and tert-butyl, and the like.

"Alkyl Acrylate" means a composition of matter defining an alkyl ester of the formula $CH_2=CHOO$-alkyl.

"Alkylene" means a divalent group derived from a straight or branched chain saturated hydrocarbon by the removal of two hydrogen atoms. Representative alkylene include methylene, 1,2-ethylene, 1,1-ethylene, 1,3-propylene, 2,2-dimethylpropylene, and the like.

"Continuously Adding" means adding at least one composition of matter to a continuous reaction.

"Continuous Reaction" means an ongoing chemical process, which is capable of continuing over an unlimited period of time in which reagents can be continuously fed into a reaction operation to continuously produce product. Continuous Process and Batch Process are mutually exclusive.

"Evaporator" means a device constructed and arranged to convert a pure liquid into a mixture having a high vapor to liquid ratio in a matter of seconds.

In at least one embodiment, a transesterification reaction is conducted to produce a N,N-dimethylaminoethyl acrylate (hereinafter DMAEA) from an alkyl acrylate. The alkyl acrylate may have from 1 to 4 carbons on the alkyl group. In at least one embodiment the reaction follows Equation I in which methyl acrylate (MA) reacts with N,N-dimethylaminoethanol (DMAE) to produce N,N-dimethylaminoethyl acrylate (DMAEA).

Equation I

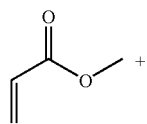

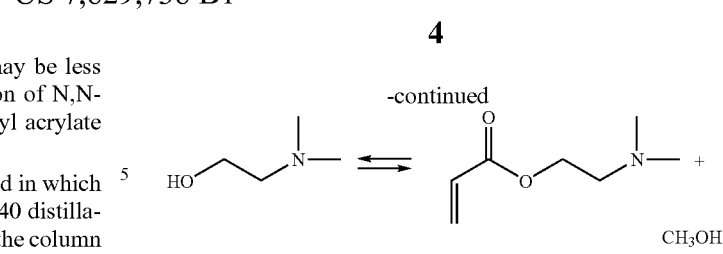

In at least one embodiment the reaction follows Equation II in which an ethyl acrylate (EA) reacts with N,N-dimethylaminoethanol (DMAE) to produce N,N-dimethylaminoethyl acrylate (DMAEA).

Equation II

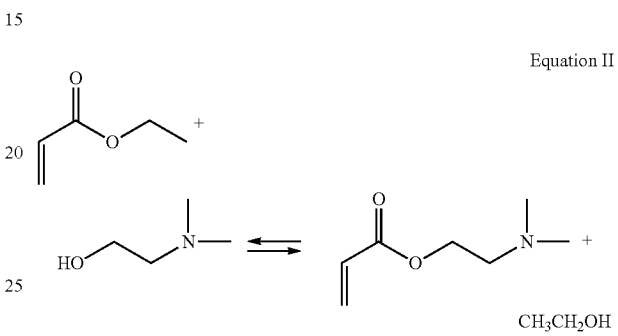

Referring now to FIG. 1. there is shown an apparatus in which the DMAEA product (1) is produced via a transesterification conducted according to a reactive distillation process. In the reactive distillation process the transesterification actually takes place within a single distillation reactor (10). The apparatus as a whole comprises a reactive distillation section (2), a purification section (3), and an entrainer recovery section (4). Reagents, entrainers, and catalysts are added via sources. DMAE is added to the system via a DMAE source (6). An alkyl acrylate is added to the system via an alkyl acrylate source (7). One or more catalysts is fed into the system via one or more catalyst sources (8). An entrainer is also added to the system via an entrainer source (5).

In at least one embodiment the catalyst is one selected from the list consisting of strong acids (such as sulfuric acid, p-toluenesulfonic acid), strong bases (such as KOH, NaOH), tin-based Lewis acids (such as di-N-butyltin oxide, dioctyltin oxide, di-N-butyltin dioxide, d-N-butyltin diacetate (DBTA), di-N-butyltin maleate, di-N-butyltin dilaurate, and di-N-butyltin dimethoxide, as well as other dialkyl tin oxides, tin carboxylates, tin alkoxides, di-alkyl stannanes, di-aryl stannanes, tri-alkyl stannanes, tri-aryl stannanes, distannoxanes, and tin (IV) chloride), titanium based Lewis acids (such as (tetraethyltitanate) tetraisopropyl titanate, tertbutyl titanate, tetra(N,N-dimethylaminoethoxy)titanate, alkoxytitanates, and tin catalysts that exist as liquids at room temperature and which are highly soluble in the reaction medium), and any combination thereof.

The entrainer azeotropically removes alcohol co-products formed during the transesterification reaction. In at least one embodiment the entrainer is a liquid. In at least one embodiment the entrainer is one selected from the list consisting of methylpentanes, hexane, heptane, C4-C8 straight chain hydrocarbons, C4-C8 cyclic hydrocarbons, C4-C8 branched hydrocarbons, and any combination thereof.

The reagents and catalysts are fed to a distillation reactor (10). In at least one embodiment the distillation reactor (10) comprises a distillation column, a reboiler (19), and a condenser (12). In at least one embodiment, the reboiler (19) is a kettle reboiler. Both the reboiler (19) and condenser (12) are in fluidic communication with the distillation column. In at least one embodiment at least a portion of the reboiler (19) is beneath at least a portion of the distillation column.

In at least one embodiment there are from 1 to 60 distillation trays are positioned in vertical sequence along the distillation column. In at least one embodiment some or all of the catalyst, DMAE, and/or entrainer are added to the same tray within the distillation reactor (10). In at least one embodiment the catalyst, DMAE and entrainer are fed to the distillation reactor (10) via a single port (11). In at least one embodiment, at least one of the catalyst, DMAE, and entrainer are fed to a tray located between the first and the 20th tray counting from the bottom tray of the distillation column (10). In at least one embodiment the distillation bottoms (21), which includes alkyl acrylate is fed into the reboiler (19). In at least one embodiment the respective feed rates of entrainer, DMAE, catalyst, and alkyl acrylate are set to a ratio of 0.935/1.00/0.030/1.451.

In at least one embodiment, the entrainer forms a volatile azeotrope distillation. In a volatile azeotrope distillation, the alcohol co-product forms an azeotrope with the entrainer, which forms a distinct distillation fraction. This azeotrope is more volatile than the other materials within the column and as a result this azeotrope has the strongest tendency to travel up the column. As a result alcohol with entrainer are substantially the only items that move upwards to the top of the distillation column under certain conditions.

This volatile azeotrope distillation is substantially different from the prior art uses of entrainers in continuous esterification processes. For example, WO 2007/057120 A1 describes an extractive distillation method. In an extractive distillation, the entrainer is not a part of a volatile azeotrope with alcohol. As a result, the alcohol travels up the column without the entrainer accompanying it. This is because the entrainer is instead kept in contact with the MA and is used to suppress the volatility of the MA and thereby prevent its forming of an azeotrope with the alcohol co-products.

The inventive volatile azeotrope method is accomplished by using different methodologies and chemicals than are used in extractive distillation. Extractive distillation makes use of volatility suppressing entrainers such as dibenzyl ether, diethylene glycol dibutyl ether, diethylene glycol di-n-butyl ether, triethylene glycol dibutyl ether, diethylene glycol diethyl ether, and tripropylene glycol dimethyl ether. In contrast, the inventive volatile azeotrope method makes use of at least one azeotrope forming entrainer, which does not suppress volatility. The thermodynamic differences between these two methods result in far less entrainer and catalyst needed per unit of alkyl acrylate. In addition, the bottoms product (13) is not contaminated with large amounts of entrainer.

Because the entire transesterification reaction is occurring within a single distillation reactor (10), the reaction may be conducted under continuous reaction conditions. As a continuous reaction, additional amounts of entrainer, DMAE, catalyst, and alkyl acrylate may be added continuously to create more DMAEA product without waiting for a first batch to complete its reaction. Furthermore the addition rates of entrainer, DMAE, catalyst, and/or alkyl acrylate, are varied in order to fine-tune the reaction while it is still running.

In addition, by conducting the transesterification reaction in a single distillation reactor (10) the process is highly efficient and can be performed using lower amounts of alkyl acrylate and entrainer relative to the amount of DMAE than is feasible using prior art methods. Lastly because the reaction occurs in a single distillation reactor, it allows for simultaneous removal of alcohol co-products and addition of more reagents and/or catalysts which makes the reaction conversion highly favorable. In at least one embodiment a high conversion is achieved even with a low ratio of alkyl acrylate to DMAE of less than 1.5. In at least one embodiment a high conversion is achieved even with a low amount of catalyst (<2.5 weight percent of DMAE). In at least one embodiment, the temperature of the bottom stream of the distillation reactor (10) distillation column is between 190° F. and 205° F.

In the purification section (3), the bottoms product (13) of the distillation reactor (10) is fed to a purification distillation column (20) equipped with a heat exchanger (15). The bottoms product (13) are the crude product of the distillation reactor (10) and are fed to the purification distillation column (20), which separates out excess and unreacted raw materials (14) for recycling and feeds them back to the distillation reactor (10). The recycled materials (14) include alkyl acrylates and N,N-dimethylaminoethanol. The bottoms of the purification distillation column (20) contains crude DMAEA.

The distilled bottoms of the purification distillation column (20) pass on to a final distillation column (23). The final distillation column (23) is in fluidic communication with an evaporator (9). The evaporator (9) separates the catalysts and heavy co-products from the DMAEA product and functions as a reboiler for the final distillation column (23). Purified DMAEA product (1) is collected as the distillate from the final distillation column (23). At least some of the bottoms (16) of the evaporator (9) which may comprise DMAEA, catalyst, and high boiling point impurities are recycled back to the distillation reactor (10). In at least one embodiment, the DMAEA product (1) is stabilized with a free-radical polymerization inhibitor (24) such as the methyl ether of hydroquinone (MEHQ).

The entrainer recovery section (4) receives the distillate (17) from the condenser (12). A separation apparatus (18) is used to separate the alcohol co-product from the entrainer (22). The invention encompasses any and all of the many methods of recovering entrainer known in the art. In at least one embodiment the separation apparatus (18) also removes recycled water and salts.

In at least one embodiment, the feed mole ratio of alkyl acrylate to DMAEA is 1.1 to 2.0. In at least one embodiment, the temperature within the reboiler (19) is between 85 C and 120 C preferably <100 C and most preferably <95 C. In at least one embodiment, the weight percentage of catalyst relative to DMAE is <5% and preferably <3%.

The foregoing may be better understood by reference to the following examples, which are presented for purposes of illustration and are not intended to limit the scope of the invention.

Example 1

Preparation of N,N-Dimethylaminoethyl Acrylate by Reactive Distillation

A stainless steel pilot scale reactive distillation unit was employed for this example. It consisted of a distillation column of 15.4 cm internal diameter with 35 sieve trays spaced 15.2 cm apart. The associated components included a condenser and accumulator to condense and return a portion of the overhead condensate, and a kettle reboiler of standard configuration to supply heat to the unit. A solution comprised of 51 parts DMAE reactant, 47.5 parts hexane entrainer, and 1.5 parts DBTA catalyst was added continuously at a rate of about 10.5 pounds per hour to the fifth plate from the bottom of the distillation column. Simultaneously, methyl acrylate (MA) reactant was added at a rate of about 7.75 pounds per hour to the reboiler, representing an MA/DMAE molar feed ratio of 1.5:1. The methanol co-product was removed from the distillation column and condensed in a heat exchanger as a hexane/methanol azeotrope. The distillate was collected from the top of the column at a rate of about 7.4 pounds per hour, and at a column head pressure of about 14.2 psia. The DMAEA product was removed from the system, along with any unreacted MA and DMAE, from the bottom of the system. The bottoms were withdrawn from the reboiler at a rate of about 11.0 pounds per hour. The temperature of the contents of the reboiler were about 92 degrees Celsius.

The distillate was comprised primarily of hexane and methanol, containing less than two weight percent methyl acrylate impurity. About ninety five percent of the condensed distillate was returned to the column (reflux ratio=20). A methanolic solution of 4-hydroxy-2,2,6,6-tetramethylpiperidinyloxy free radical inhibitor was added to the condensed distillate in an amount sufficient to provide 100 ppm inhibitor concentration in the condensed distillate returned to the distillation column in order to help prevent polymerization in the column.

The bottoms withdrawn from the reboiler primarily comprised the desired DMAEA product and the excess MA that was added to the reactor. In addition, the bottoms were contaminated with percent levels of unreacted DMAE and catalyst, along with smaller amounts of methanol, hexane, and heavy impurities. The GC analyses of the bottoms, which represent the crude product of the reactive distillation process, are shown in table 1. In this example, a 94 mole percent conversion of DMAE to DMAEA was achieved under mild reaction conditions that produced very low levels of heavy volatile impurities.

Examples 2-7

Preparation of N,N-Dimethylaminoethyl Acrylate by Reactive Distillation

DMAEA was produced as described above in Example 1, except that the process conditions were varied as described in the table below. The process variables included the MA/DMAE molar feed ratio (MA/DMAE), the weight percent catalyst based on the total weight of DMAE reactant (wt. % Cat), the percent reaction conversion of DMAE to DMAEA (% Cony.) based on the GC analysis described below, the bottoms temperature ($T_B$ (°C.)), and the residence time in the reboiler expressed in hours (Res. Time (h)). In general, a high chemical conversion of the limiting DMAE reactant to the desired DMAEA product could be achieved under desirable process conditions (low MA/DMAE feed ratios, a low amount of catalyst, and a low reboiler temperature (<100 C)). The volatile components of bottoms samples representative of the experimental process conditions are measured by gas chromatography (GC) and the results are listed under the "Volatile Components" heading in the table. The bottoms compositions from examples 1 and 2 illustrate the achievement of a high DMAEA concentration (>60 wt. %), a high DMAE conversion (>85 mole %), and a low impurity level (<1 wt. %) in the bottoms. The results from examples 5 and 7 confirm that high DMAE conversions (>90%) and low levels of byproduct (<1%) can be achieved with relatively low MA/DMAE feed ratios of 1.6 (Example 6) or 1.7 (Example 7). Example 3 illustrates that the MA/DMAE feed ratio can be desirably reduced even further (down to 1.2 in Example 3), but the reboiler temperature will increase to greater than 100 C in this case, and this will result in a higher level of impurities. Examples 4 and 6 illustrate that if the reboiler residence time is reduced to about 2 hours, the chemical conversion of DMAE to DMAEA will suffer.

TABLE 1

| | Process Conditions | | | | | Volatile Components (wt %) | | | | | |
|---|---|---|---|---|---|---|---|---|---|---|---|
| Example | MA/ DMAE | wt % Cat | % Conv. | TB (°C.) | Res. Time(h) | DMAEA | MA | DMAE | MeOH | Hexane | Impurities |
| 1 | 1.5 | 3 | 94 | 92 | 4.5 | 69.5 | 24.7 | 2.9 | 0.27 | 2.6 | 0 |
| 2 | 1.5 | 2 | 88 | 91 | 5 | 68.1 | 22.2 | 5.8 | 0.28 | 3.2 | 0.42 |
| 3 | 1.2 | 2 | 93 | 102 | 5 | 79.2 | 15.2 | 3.5 | 0.17 | 1.0 | 1.02 |
| 4 | 1.2 | 4 | 75 | 88 | 2.3 | 59.4 | 23.8 | 12.0 | 0.51 | 4.2 | 0.2 |
| 5 | 1.6 | 4 | 91 | 87 | 3.9 | 57.8 | 35.9 | 2.8 | 0.23 | 3.2 | 0.14 |
| 6 | 1.6 | 4 | 72 | 82 | 1.8 | 50.4 | 30.1 | 12.1 | 0.38 | 6.9 | 0.13 |
| 7 | 1.7 | 4 | 91 | 85 | 3.7 | 57.8 | 34.3 | 3.6 | 0.27 | 4.0 | 0 |

While this invention may be embodied in many different forms, there are shown in the drawings and described in detail herein specific preferred embodiments of the invention. The present disclosure is an exemplification of the principles of the invention and is not intended to limit the invention to the particular embodiments illustrated. Furthermore, the invention encompasses any and all possible combinations of some or all of the various embodiments described herein. Any and all patents, patent applications, scientific papers, and other references cited in this application are hereby incorporated by reference in their entirety.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method of preparing a N,N-dialkylaminoalkyl acrylate of Formula 1:

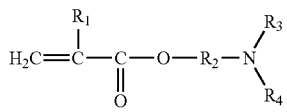

(Formula 1)

wherein $R_1$ is H, or $C_1$-$C_4$ alkyl; $R_2$ is $C_1$-$C_4$ alkylene; and $R_3$ and $R_4$ are $C_1$-$C_4$ alkyl, comprising:
 a) providing a distillation reactor comprising a distillation column and a reboiler;
 b) continuously adding to the distillation column, entrainer, catalyst, polymerization inhibitor, and an alkyl acrylate of Formula 2

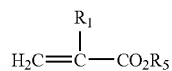

(Formula 2)

wherein $R_5$ is $C_1$-$C_4$ alkyl and a dialkylamino alcohol of Formula 3

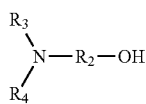

(Formula 3)

under conditions resulting in the transesterification of the alkyl acrylate with said dialkylamino alcohol to form said N,N-dialkylaminoalkyl acrylate and an alcohol of formula $R_5OH$; and
 c) simultaneously removing an azeotropic mixture of the entrainer and the alcohol from the distillation column and removing the N,N-dialkylaminoalkyl acrylate from the reboiler.

2. The method of claim 1 wherein $R_1$ is H or methyl, $R_2$ is ethylene and $R_3$, $R_4$ and $R_5$ are methyl.

3. The method of claim 2 in which the entrainer is selected from the list consisting of methylpentane, hexane, heptane, C4-C8 straight chain hydrocarbons, C4-C8 cyclic hydrocarbons, C4-C8 branched hydrocarbons, and any combination thereof.

4. The method of claim 3 wherein the catalyst is one item selected from the list consisting of strong acids, strong bases, tin-based Lewis acids, titanium based Lewis acids, and tin catalysts that exist as liquids at room temperature and which are highly soluble in the reaction medium, DBTA, and any combination thereof.

5. The method of claim 4 wherein the entrainer, catalyst, inhibitor, dialkylamino alcohol and alkyl acrylate are added to the reboiler.

6. The method of claim 4 wherein the entrainer, catalyst, inhibitor and dialkylamino alcohol are added to the distillation column and the alkyl acrylate is added to the reboiler.

7. The method of claim 1 wherein the distillation column comprises between 1 and 60 distillation trays arranged sequentially from a bottom of the column to a top of a column.

8. The method of claim 7 wherein one item selected from the list of the entrainer, the catalyst, and the inhibitor are fed into the distillation column at a position lower than a middlemost distillation tray.

9. The method of claim 4 where $R_1$ is H, the molar feed ratio of methyl acrylate to N,N-dimethylaminoethanol is less than or equal to 1.7, and the chemical conversion of N,N-dimethylaminoethanol to N,N-dimethylaminoethyl acrylate is greater than 88%.

10. The method of claim 1 in which there is substantially no entrainer mixed with the N,N-dialkylaminoalkyl acrylate when the N,N-dialkylaminoalkyl acrylate is removed from the reboiler.

11. The method of claim 10 in which the pressure within the distillation column is within the range of 14-14.4 psia.

12. The method of claim 1 in which the reboiler is a kettle reboiler.

* * * * *